United States Patent
Katou

(10) Patent No.: US 9,795,360 B2
(45) Date of Patent: Oct. 24, 2017

(54) ULTRASOUND PROBE

(71) Applicant: KONICA MINOLTA, INC., Chiyoda-ku, Tokyo (JP)

(72) Inventor: Yoshiki Katou, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 32 days.

(21) Appl. No.: 14/208,517

(22) Filed: Mar. 13, 2014

(65) Prior Publication Data

US 2014/0194739 A1 Jul. 10, 2014

Related U.S. Application Data

(62) Division of application No. 13/486,279, filed on Jun. 1, 2012, now abandoned.

(30) Foreign Application Priority Data

Jun. 7, 2011 (JP) .................................. 2011-126856

(51) Int. Cl.
*A61B 8/00* (2006.01)
*A61B 8/14* (2006.01)
*G01S 7/00* (2006.01)
*G01S 7/52* (2006.01)

(52) U.S. Cl.
CPC ............ *A61B 8/145* (2013.01); *A61B 8/4405* (2013.01); *A61B 8/4472* (2013.01); *A61B 8/4483* (2013.01); *A61B 8/56* (2013.01); *G01S 7/5208* (2013.01); *A61B 8/461* (2013.01); *A61B 8/467* (2013.01); *G01S 7/003* (2013.01); *G01S 7/52096* (2013.01)

(58) Field of Classification Search
None
See application file for complete search history.

(56) References Cited

U.S. PATENT DOCUMENTS

| 2009/0274347 A1* | 11/2009 | Gat | A61B 1/00036 |
| | | | 382/128 |
| 2009/0299185 A1* | 12/2009 | Oikawa | A61B 8/14 |
| | | | 600/447 |
| 2010/0312114 A1* | 12/2010 | Karasawa | A61B 8/14 |
| | | | 600/447 |
| 2011/0028859 A1* | 2/2011 | Chian | A61B 5/04001 |
| | | | 600/554 |

FOREIGN PATENT DOCUMENTS

JP 2009-291515 A 12/2009

\* cited by examiner

*Primary Examiner* — Tse Chen
*Assistant Examiner* — Jason Ip
(74) *Attorney, Agent, or Firm* — Holtz, Holtz & Volek PC

(57) ABSTRACT

An ultrasound probe includes a receiving section to receive ultrasound waves from an object and to acquire a receiving signal of each of multiple channels; a beam forming section to adjust a phase of the receiving signal of each of multiple channels and to sum the receiving signals; an image producing section to produce image data to display an ultrasound diagnostic image based on the receiving signals summed by the beam forming section; a transmission target selecting section to select one from at least two of the receiving signal for each of multiple channels, the receiving signals summed by the beam forming section, and the image data as a transmission target; and a transmitting section to transmit the transmission target selected by the transmission target selecting section.

16 Claims, 3 Drawing Sheets

ULTRASOUND PROBE

This is a Divisional of U.S. application Ser. No. 13/486,279, filed Jun. 1, 2012, which is based on Japanese Patent Application No. 2011-126856, filed Jun. 7, 2011, the entire contents of both of which are incorporated herein by reference.

BACKGROUND OF THE INVENTION

The present invention relates to an ultrasound probe.

Conventionally, known ultrasound image diagnostic apparatuses of a wireless type are configured to wirelessly transmit ultrasound wave data acquired by an ultrasound probe to an apparatus main body.

In such an ultrasound image diagnostic apparatus, an ultrasound probe being a transmission source converts the acquired ultrasound wave data into a prescribed data format capable of being processed in an apparatus body being a transmission destination, and then the converted ultrasound wave data are transmitted to the apparatus main body (for example, refer to Japanese Unexamined Patent Publication No. 2009-291515).

However, in the technique described in the above patent document, the data format transmitted by the ultrasound probe is predetermined in accordance with the specification of the device body being a transmission destination. Accordingly, the ultrasound probe deals with only the above device body or a device body with the equivalent specification. Therefore, the ultrasound probe is poor in general versatility.

SUMMARY OF THE INVENTION

An object of the present invention is to provide an ultrasound probe which can be applied to ultrasound image diagnostic apparatuses with various specifications and has high general versatility.

In order to solve the above problems, in the invention described in Item 1, an ultrasound probe includes:

a receiving section to receive ultrasound waves from an object and to acquire a receiving signal of each of multiple channels;

a phasing and adding section to perform processing of phasing and adding for the receiving signal of each of multiple channels;

an image producing section to produce image data to display an ultrasound diagnostic image based on the receiving signals having been subjected to the processing of phasing and adding;

a transmission target selecting section to select one from at least two of the receiving signal for each of multiple channels, the receiving signals having been subjected to the processing of phasing and adding, and the image data as a transmission target; and a transmitting section to transmit the transmission target selected by the transmission target selecting section.

In the invention described in Item 2, in the ultrasound probe described in Item 1, the ultrasound probe further includes a changeover switch to allow an operator to perform changeover operations, and the transmission target selecting section selects the transmission target in accordance with an operation via the changeover switch.

In the invention described in Item 3, in the ultrasound probe described in Item 1, the ultrasound probe further includes a battery as a power source to make respective sections of the ultrasound probe to act, and the transmission target selecting section selects the transmission target in accordance with a remaining quantity of electricity in the battery.

In the invention described in Item 4, in the ultrasound probe described in Item 1, the transmission target selecting section selects the transmission target in accordance with a transmitting condition between the transmitting section and an ultrasound image diagnostic apparatus body which is a transmission destination of the transmission target.

In the invention described in Item 5, in the ultrasound probe described in Item 1, the ultrasound probe further includes a transmission signal receiving section to receive a transmission signal from an ultrasound image diagnostic apparatus body which is a transmission destination of the transmission target, and when the transmission signal receiving section receives a transmission target designating signal to designate a transmission target from the ultrasound image diagnostic apparatus body, the transmission target selecting section selects the transmission target corresponding to the received transmission target designating signal.

In the invention described in Item 6, in the ultrasound probe described in any one of Items 1 to 5, the ultrasound probe further includes a power control section to select a limiting target, to which supply of power is limited, from the phasing and adding section and the image producing section based on the transmission target selected by the transmission target selecting section, and to limit supply of power for the selected limiting target.

In the invention described in Item 7, in the ultrasound probe described in any one of Items 1 to 5, the ultrasound probe further includes an operation clock control section to select a lowering target, to which a frequency of an operation clock is lowered, from the phasing and adding section and the image producing section based on the transmission target selected by the transmission target selecting section, and to change a frequency of an operation clock supplied to the selected lowering target from a prescribed driving frequency to a prescribed standby frequency being a lower frequency than the driving frequency.

According to the present invention, an ultrasound probe can be configured to be applied to ultrasound image diagnostic apparatuses with various specifications and to have high general versatility.

DETAILED DESCRIPTION OF THE PREFERRED EMBODIMENT

Figure 1:
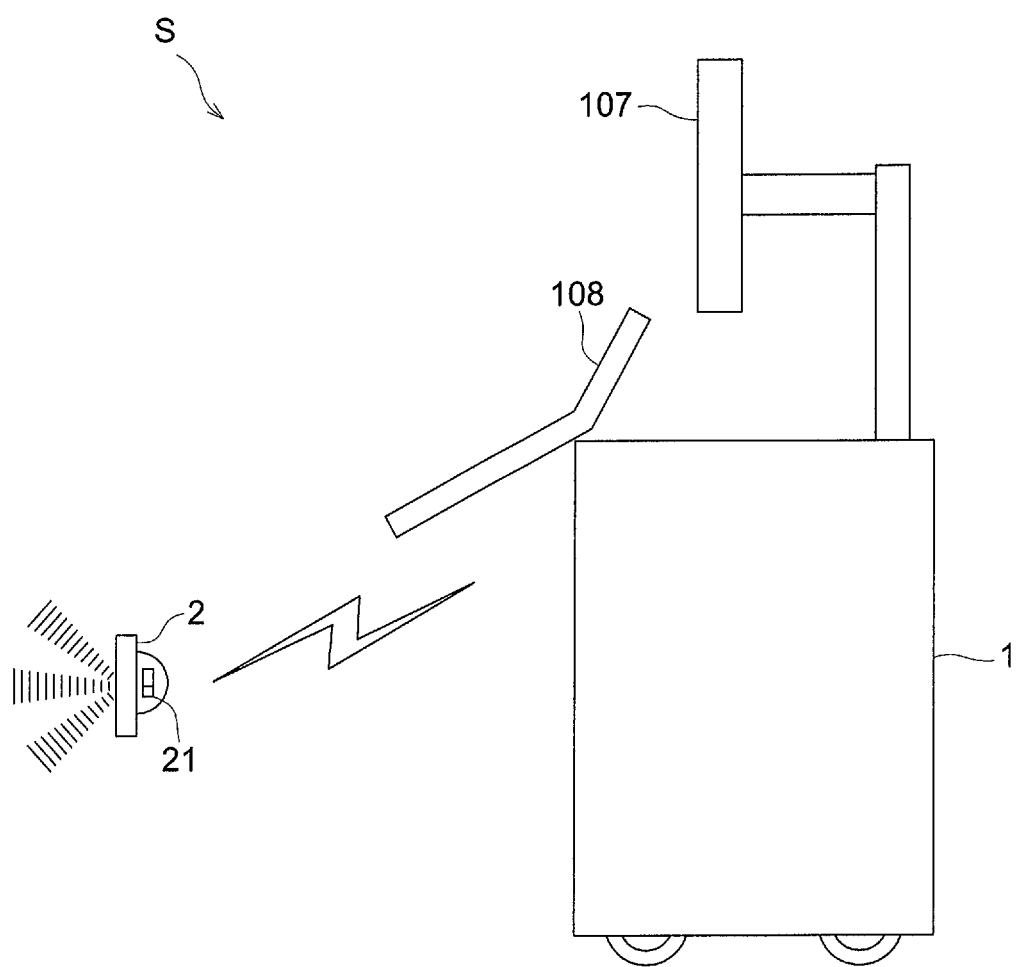
FIG. 1 is a diagram illustrating an outer appearance constitution of an ultrasound image diagnostic apparatus.

Hereafter, an ultrasound diagnostic apparatus according to the embodiment of the present invention will be explained with reference to a drawing. However, the scope of the invention is not limited to the examples shown in the drawings. In the following description, structural parts which have the same function and structure to each other are provided with the same reference symbols, and the description for them will be omitted.

As shown in FIG. 1, an ultrasound image diagnostic apparatus S according to an embodiment of the present invention includes an ultrasound image diagnostic apparatus main body 1 and a ultrasound probe 2. The ultrasound probe 2 is configured to transmit ultrasound waves (transmitted ultrasound waves) to samples, such as a living body which is not illustrated, and to receive reflected waves (reflected ultrasound waves: echo) of the ultrasound waves reflected from this sample. Further, the ultrasound probe 2 is configured to be able to transmit and receive data wirelessly to and from the ultrasound image diagnostic apparatus main body 1. As wireless communication systems, any known systems may be employable. However, in this embodiment, for examples, a system according to an international standard "IEEE802.11n" is employed. The ultrasound probe 2 is configured to acquire reception signals being electric signals from the received reflected ultrasound waves, to convert the reception signals via A/D conversion into data with a predetermined transmission format, and then to transmit wirelessly the data to the ultrasound image diagnostic apparatus main body 1. The ultrasound probe 2 includes a changeover switch 21 to allow an operator to perform changeover operations. The changeover switch 21 is, for example, a slide switch. However, as long as an operator can perform changeover operations, any type of switches, such as limit switches, and toggle switches may be employable.

The ultrasound image diagnostic apparatus main body 1 makes an internal state of a sample images as an ultrasound diagnostic image based on the data transmitted from the ultrasound probe 2, and displays the images on a display 107. Moreover, the ultrasound image diagnostic apparatus main body 1 is equipped with the operation input section 108, and can carry out the radio transmission of the information according to actuation of the operation input section 108 to the ultrasound probe 2.

Figure 2:
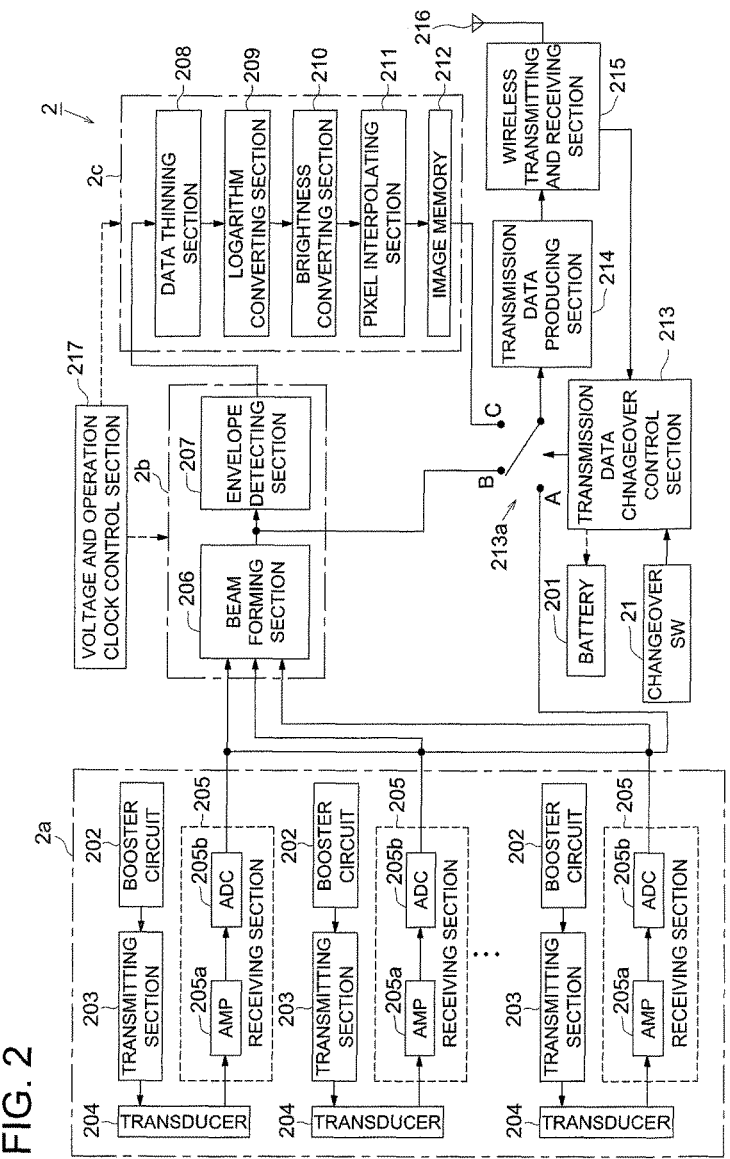
FIG. 2 is a block diagram illustrating an outline constitution of an ultrasound probe.

As shown in FIG. 2, the ultrasound probe 2 includes, for example, a battery 201, a booster circuit 202, a transmitting section 203, transducers 204, a receiving section 205, a beam forming section 206, an envelope detecting section 207, a data thinning section 208, a logarithm converting section 209, a brightness converting section 210, a pixel interpolating section 211, an image memory 212, a transmission data changeover control section 213, a transmission data producing section 214, a wireless transmission and reception section 215, an antenna 216, and a voltage and operation clock control section 217.

The battery 201 supplies a power source to respective sections which constitute the ultrasound probe 2. For example, when the ultrasound probe 2 is attached to a holder (not shown) of the ultrasound diagnostic apparatus main body 1, an electric power is supplied to the battery 201.

The booster circuit 202 is a circuit which is configured to raise a power source voltage supplied from the battery 201 to a voltage of 60 V to 150 V which can drive the ultrasound probe 2, and to supply the raised power voltage to the transmitting section 203.

The transmitting section 203 is a circuit configured to supply driving signals being electrical signals to the transducers 204, and to make the transducers 204 generate transmitting ultrasound waves. The transducer 204 is composed of, for example, a piezoelectric element, and a plurality of transducers 204 are arranged in an one dimensional array form. After outputting transmitting ultrasound waves, upon receipt of reflected ultrasound waves, the transducer 204 outputs reception signals to the receiving section 205. In this embodiment, for example, 192 transducers 204 are aligned. In this regard, the transducers may be arranged in a two-dimensional array form. Further, the number of transducers may be set up arbitrarily. Moreover, in this embodiment, although a linear electronic scan probe is adopted as the ultrasound probe 2, any type of an electronic scanning type or a mechanical scanning manner may be adopted, and further any type of a linear scan type, a sector scanning type and a convex scan type may also be adopted. The transmitting section 203 includes, for example, a transmitting BF (Beam Forming) control circuit, and sets a delay time to a transmission timing of a driving signal for each of individual passages corresponding to the respective transducers, and focus a transmission beam composed of transmission ultrasound waves by delaying transmission of respective driving signals by the set delaying time.

The receiving section 205 includes an AMP (amplifier) 205a, and an ADC (Analog to Digital Converter) 205b. A plurality of receiving sections 205 are provided corresponding to the plurality of transducers. The amplifier 205a is a circuit for amplifying the reception signals with respective predetermined amplification rates set beforehand for respective individual passages corresponding to the respective transducers. The ADC 205b is configured to conduct an A/D conversion for the amplified reception signals by sampling with a predetermined frequency (for example, 60 MHz), and output the converted reception signals.

In this embodiment, the transmitting and receiving section 2a is constituted by the booster circuit 202, the transmitting section 203, the transducers 204, and the receiving section 205 which are constituted as mentioned above.

The beam forming section 206 adjusts timing phase of the reception signals subjected to the A/D conversion by the ADC 205b by providing a delay time for each of the individual passages corresponding to the respective transducers, sums these signals so as to produce sound ray data, and outputs the sound ray data. The envelope detecting section 207 performs full wave rectification for the sound ray data output from the beam forming section 206, and obtains envelope data. The envelope detecting section 207 outputs the acquired envelope data to the data thinning section 208.

In this embodiment, a sound ray data producing section 2b is constituted by the beam forming section 206 and the envelope detecting section 207 both of which are structured as mentioned above.

The data thinning section 208 conducts data thinning with regard to a distance direction (depth direction) of the envelope data in accordance with an image size to be displayed on the display 107 of the ultrasound image diagnostic apparatus main body 1. The logarithm converting section 209 performs a logarithmic amplification to the input envelope data. At this time, adjustment of a gain, a dynamic range, and the like may be performed. The brightness converting section 210 performs an amplitude/brightness conversion in order to quantize the magnitude of signals indicated by the envelope data subjected to the logarithmic amplification into 256 gradations, thereby producing B mode image data. That is, the B mode image data expresses the strength of reception signals with brightness. The pixel interpolating section 211 produces interpolated pixel data being data of interpolating pixels arranged in the azimuth direction of the B mode image data in accordance with an image size to be displayed on the display 107 of the ultrasound image diagnostic apparatus main body 1. The image memory 212 is constituted by, for example, semiconductor memories, such as DRAM (Dynamic Random Access Memory), and stores the B mode image data and the interpolating pixel data transmitted from the pixel interpolating section 211 in a unit of a frame. That is, the image memory 212 can store the ultrasound diagnostic image data constituted in a unit of a frame.

In this embodiment, the image producing section 2c is constituted by the data thinning section 208, the logarithm converting section 209, the brightness converting section 210, the pixel interpolating section 211, and the image memory 212 which are constituted as mentioned above.

The transmission data changeover control section 213 changes over data input into the transmission data producing section 214 as a target of a radio transmission by changing over the setting position of the transmit data changeover switch 213a. Specifically, when the transmit data changeover switch 213a is set at a position "A", the transmission data changeover control section 213 inputs the reception signals of respective channels output from the ADC 205b after being subjected to the A/D conversion as a target of wireless transmission into the transmission data producing section 214. Further, when the transmit data changeover switch 213a is set at a position "B", the transmission data changeover control section 213 inputs sound ray data output from the beam forming section 206 as a target of wireless transmission into the transmission data producing section 214. Furthermore, when the transmit data changeover switch 213a is set at a position "C", the transmission data changeover control section 213 inputs ultrasound diagnostic image data as a target of wireless transmission into the transmission data producing section 214. In this way, in this embodiment, a transmission target selecting section is constituted by the transmission data changeover control section 213 and the transmit data changeover switch 213a. Here, this embodiment is constituted such that only one among switch-over conditions mentioned below is selectively functioned. However, needless to say, multiple switch-over conditions may be functioned.

The transmission data changeover control section 213 is connected to a changeover switch 21. The changeover switch 21 outputs signals corresponding to the position of the switch to the transmission data changeover control section 213. The transmission data changeover control section 213 makes a signal from the changeover switch 21 as a changeover condition, and can change the position of the transmission data changeover switch 213a in accordance with this.

Further, the transmission data changeover control section 213 is configured to detect a remaining quantity of the battery 201, makes the detection result of the remaining quantity as a changeover condition, and can change the position of the transmission data changeover switch 213a in accordance with the remaining quantity. For example, when the transmission data changeover control section 213 detects that the remaining quantity of the battery 201 becomes 60% or less, the position of the transmission data changeover switch 213a is set to "B", and when the transmission data changeover control section 213 detects that the remaining quantity of the battery 201 becomes 40% or less, the position of the transmission data changeover switch 213a is set to "A", whereby processing load is reduced so as to suppress the consumption of the battery.

The transmission data producing section 214 produces transmission data by converting the data input from the transmission data changeover switch 213a into a predetermined transmission form, and outputs the transmission data to the wireless transmission and reception section 215. At this time, in order to judge a wireless transmission state of the ultrasound image diagnostic apparatus main body 1 and the ultrasound probe 2, error correcting codes are added. In this regard, error correcting codes may be made not to be added.

The wireless transmission and reception section 215 applies a predetermined modulation process to the transmission data output from the transmission data producing section 214, and wirelessly transmits the resulting transmission data to the ultrasound image diagnostic apparatus main body 1 via the antenna 216. Further, the wireless transmission and reception section 215 receives the transmission target designating information and transmission state information both mentioned below wirelessly transmitted from the ultrasound image diagnostic apparatus main body 1 via the antenna 216, demodulates the received information, and outputs the demodulated information to the transmission data changeover control section 213.

A voltage and operation clock control section 217 acting as a power control section and an operation clock control section limits the supply of power to the sound ray data producing section 2b and the image producing section 2c, or controls the frequency of the operation clock signal supplied to the sound ray data producing section 2b and the image producing section 2c in accordance with the changeover position of the transmission data changeover switch 213a by the transmission data changeover control section 213. The voltage and operation clock control section 217 can select one of the limitation of the power supply and the control of the operation clock frequency, and conducts the selected one. In this connection, the embodiment may be made to provide only one of a power control section to limit power supply and an operation clock control section to control an operation clock frequency in place of the voltage and operation clock control section 217. Further, the embodiment may be made to provide none of the power control section and the operation clock control section.

Now, description will be given for operations in the case where supply of power is limited by the voltage and operation clock control section 217.

When the transmission data changeover switch 213a is set at the position "A" by the transmission data changeover control section 213, the voltage and the operation clock control section 217 stops supply of power to the sound ray data producing section 2b and the image producing section 2c. That is, when reception signals after being subjected to the A/D conversion are selected as a wireless transmission target by the transmission data changeover control section 213, the beam forming processing and the image production processing become unnecessary. Accordingly, with the stop of operations in respective sections to conduct the above processing, power saving may be attained.

Moreover, similarly, when the transmission data changeover switch 213a is set at the position "B" by the transmission data changeover control section 213, the sound ray data are selected as a wireless transmission target, and the image producing processing by the image producing section 2c becomes unnecessary. Accordingly, the voltage and operation clock control section 217 stops supply of power to the image producing section 2c.

Meanwhile, when the transmission data changeover switch 213a is set at the position "C" by the transmission data changeover control section 213, the voltage and operation clock control section 217 supplies power to both the sound ray data producing section 2b and the image producing section 2c.

Next, description will be given for operations in the case where control of operation clock frequency is conducted by the voltage and operation clock control section 217.

When the transmission data changeover switch 213a is set at the position "A" by the transmission data changeover control section 213, the voltage and operation clock control section 217 changes the frequency of the operation clock signal supplied to the sound ray data producing section 2b and the image producing. section 2c from the usual drive frequency to the standby frequency being a lower frequency than the drive frequency. Specifically, for example, the above change can be realized by change over clock signals output from a crystal oscillator from a frequency divider circuit for the usual driver to a frequency divider circuit for standby. For example, the standby frequency may set to ½ to ⅛ of the drive frequency. However, the standby frequency is not limited to this example. By the above constitution, power saving may be attained.

Further, similarly, when the transmission data changeover switch 213a is set at the position "B" by the transmission data changeover control section 213, the voltage and operation clock control section 217 changes the frequency of the operation clock signal supplied to the image producing section 2c from the usual drive frequency to the standby frequency.

Meanwhile, when the transmission data changeover switch 213a is set at the position "C" by the transmission data changeover control section 213, the voltage and operation clock control section 217 makes the frequency of the operation clock signal supplied to both the sound ray data producing section 2b and the image producing section 2c to the usual drive frequency.

Figure 3:
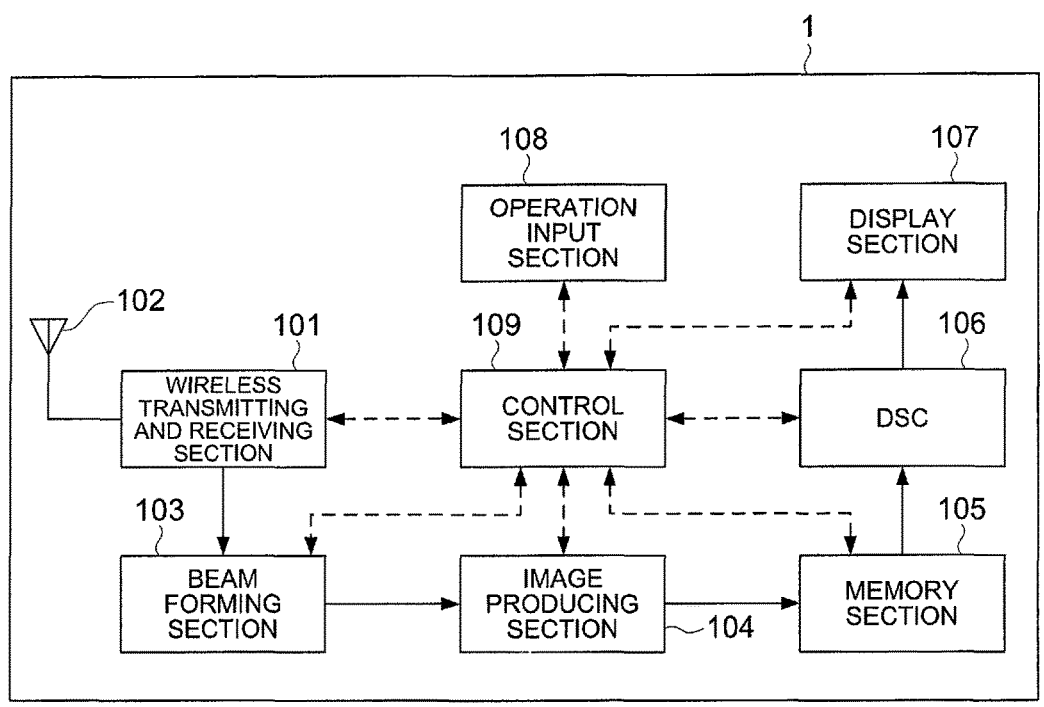
FIG. 3 is a block diagram illustrating an outline constitution of an ultrasound image diagnostic apparatus main body.

As shown in FIG. 3, the ultrasound image diagnostic apparatus main body 1 includes, for example, a wireless transmission and reception section 101, an antenna 102, a beam forming section 103, an image producing section 104, a memory section 105, a DSC(Digital Scan Converter)106, a display 107, an operation input section 108, and a control section 109.

The control section 109 includes, for example, a CPU (Central Processing Unit), a ROM (Read Only Memory) and a RAM (Random Access Memory). The control section 109 reads out various processing programs, such as a system program memorized in the ROM, develops the processing programs to the RAM, and conduct central control for operations of respective sections of the ultrasound image diagnostic apparatus S in accordance with the developed programs.

The ROM is constituted by nonvolatile memories, such as semi-conductor memories, etc. and memorizes system programs corresponding to the ultrasound image diagnostic apparatus S, various processing programs capable of being executed on the system programs, and various data. These programs are stored with the form of program codes readable by a computer, and the CPU performs operations sequentially in accordance with the program code. The RAM forms a work area in which various programs executed by the CPU and data in association with these programs are stored temporarily.

In accordance with instruction of the control section 109, the wireless transmission and reception section 101 receives transmission data wirelessly transmitted from the ultrasound probe 2 and demodulates the data. When the received transmission data are reception signals of respective channels after being subjected to the A/D conversion, the control section 109 instructs the wireless transmission and reception section 101 so as to output the demodulated transmission data to the beam forming section 103. Further, when the received transmission data are sound ray data, the control section 109 instructs the wireless transmission and reception section 101 so as to output the demodulated transmission data to the image producing section 104. Furthermore, when the received transmission data are ultrasound diagnostic image data, the control section 109 instructs the wireless transmission and reception section 101 so as to output the demodulated transmission data to the memory section 105.

Moreover, the wireless transmission and reception section 101 outputs the received transmission data to the control section 109. The control section 109 calculates the error ratio of data based on the error correcting code added to this transmission data. Here, an error ratio is an index which shows how many data are in error in transmission data when the transmission data transmitted wirelessly from the ultrasound probe 2 are received by the ultrasound image diagnostic apparatus main body 1 That is, the error ratio is a value which shows a ratio which transmission data are in error during the wireless transmission from the ultrasound probe 2 to the ultrasound image diagnostic apparatus main body 1 The control section 109 judges the transmission state between the ultrasound image diagnostic apparatus main body 1 and the ultrasound probe 2 from the calculated error ratio. The transmission state is set, for example as three stages. The control section 109 instructs the wireless transmission and reception section 101 to wirelessly transmit transmission state information indicating the judged transmission state to the ultrasound probe 2 via the antenna 102. The ultrasound probe 2 makes the received transmission state information as a changeover condition and conducts control in accordance with the received transmission state information. For example, when the transmission state information is information indicating that the transmission state is good, the ultrasound probe 2 controls the transmission data changeover control section 213 to change over the position of the transmission data changeover switch 213a to "A". Further, when the transmission state information is information indicating that the transmission state is not good, the ultrasound probe 2 controls the transmission data changeover control section 213 to change over the position of the transmission data changeover switch 213a to "B". Furthermore, when the transmission state information is information indicating that the transmission state is bad, the ultrasound probe 2 controls the transmission data changeover control section 213 to change over the position of the transmission data changeover switch 213a to "C" in accordance with the transmission state information. In this case, further, the remaining quantity of the battery 201 mentioned above is detected by the transmission data changeover control section 213, and the position of the transmission data changeover switch 213a may be changed over in accordance with the remaining quantity. In addition, the control section 109 may be made to perform the error correction of the transmission data based on the error correcting code added to the transmission data.

The beam forming section 103 performs beam forming for the reception signals of respective channels after being subjected to the A/D conversion so as to produce sound ray data, and outputs the sound ray data to the image producing section 104. Since the procedures of the beam forming are same those in the beam forming section 206 of the ultrasound probe 2, the detailed description about the procedures of the beam forming are omitted.

The image producing unit 104 conducts envelope detection processing, a logarithmic amplification, etc. for the sound ray data produced by the beam forming section 103 and the ultrasound probe 2, and further conducts the adjustment of a *mule range and gain so as to convert the brightness, thereby producing B-mode image data Subsequently, the B-mode image data produced in the above ways are transmitted to the memory unit 105.

The memory unit 105 is constituted by, for example, semiconductor memories, such as a DRAM, and memorizes the B-mode image data transmitted from the image producing unit 104 in a unit of a frame. With this, ultrasound diagnostic image data are produced. Further, the memory unit 105 can memorize ultrasound diagnostic image data produced in the ultrasound probe 2 in a unit of a frame. Subsequently, the memorized ultrasound diagnostic image data in the memory unit 105 is transmitted to the DSC 106 in accordance with control of the control unit 109.

The DSC 106 converts the ultrasound diagnostic image data received from the memory unit 105 into image signals corresponding to the scan mode by television signals, and outputs them to the display unit 107.

As the display unit 107, displays, such as a LCD (Liquid Crystal Display), a CRT (Cathode-Ray Tube) display, an organic electroluminescence (Electronic Luminescence) display, and a plasma display may be applicable. The display unit 107 displays images on a display screen in accordance with the image signals output from the DSC 106. In this connection, in replace of a display device, printing devices such as printers may be employed.

The operation inputting unit 108 is equipped with various types of switches, buttons, trackballs, mouse, and keyboards, for example, for performing input of commands to instruct start of diagnosis and data with regard to personal information of objects to be examined, and the operation inputting unit 108 outputs operation signals to the control unit 109. A user can select the target of data wirelessly transmitted from the ultrasound probe 2 via operations on the operation input section 108. The control section 109 instructs in accordance with selection operation on the operation inputting unit 108 the wireless transmission and reception section 101 to wirelessly transmit the transmission target designating information to designate data to be made as a target of wireless transmission to the ultrasound probe 2 via the antenna 102. The ultrasound probe 2 makes the received transmission target designating information as a changeover condition, and can change over the position of the transmission data changeover switch 213a by the transmission data changeover control section 213 in accordance with the received transmission target designating information.

The usability of the ultrasound probe 2 constituted in the above way will be described.

As shown in FIG. 2, the reception data for each channel having been subjected to the A/D conversion, the sound ray data, and the ultrasound diagnostic image data are different in data format from each other, and further different in data size from each other. Therefore, they are also different in required transmission rate. For example, consideration is taken for the case where the reception data having been subjected to the A/D conversion of each channel are transmitted wirelessly from the ultrasound probe 2 to the ultrasound image diagnostic apparatus main body 1. In the above case, when the number of channels is 192 CHs, the reception data having been subjected to the A/D conversion per one channel are quantized into 14 bits and the sampling frequency of reception signals is 60 MHz, an at least necessary transmission rate becomes as follows.

$$192 \times 14 \times 60 \times 10^6 = 161.28 \text{ Gbps}$$

Further, the reception signals of each channel are subjected to the beam forming process, and in the case where the sound ray data of 22 bit per one sample are wirelessly transmitted, an at least necessary transmission rate becomes as follows.

$$22 \times 60 \times 10^6 = 1320 \text{ Mbps}$$

Furthermore, consideration is taken for the case where ultrasound diagnostic image data are produced based on the sound ray data and the resulting ultrasound diagnostic image data are wirelessly transmitted. In the above case, on the supposition that a screen size is set to vertical×horizontal: 1000 dot×1000 dot, data size per one dot is set to 24 bit (8 bit for each of RGB) in order to correspond to color Doppler method, and a frame rate is set to 15 Frame/sec, an at least necessary transmission rate becomes as follows.

$$24 \times 1000 \times 1000 \times 15 = 360 \text{ Mbps}$$

That is, if wireless transmission is conducted by use of ultrasound diagnostic image data, the necessary transmission rate becomes the smallest.

On the other hand, with regard to processing for reception signals, such as a beam forming process, an envelope detection process, a data thinning process, and a pixel interpolation process, various techniques are applied on an apparatus by manufacturers of ultrasound image diagnostic apparatus main body and product models in order to distinguish from other apparatuses. As mentioned above, in the ultrasound probe 2, the reception signals are processed to be made to ultrasound diagnostic image data, and then the ultrasound diagnostic image data are wirelessly transmitted. This technique becomes advantageous in respect of a transmission rate. However, in the ultrasound image diagnostic apparatus main body-side, there is no chance to apply the above-mentioned signal processing technique to the reception signals. Such advantages on the apparatus main body side are not utilized. Accordingly, for example, in the case where data can be transmitted with a data format such as reception signal of each channel to which the above-mentioned signal processing technique can be applied, although a necessary transmission rate becomes large, the degree of freedom in terms of signal processing at the apparatus main body side increases, and the ultrasound probe is made excellent in usability.

Moreover, as the number of processing processes for reception signals increases, hardware resources used for the processing increases and power consumption increases. For example, in the ultrasound probe 2 in this embodiment, when a processing load on the entire constitution shown in FIG. 2 is 100%, a processing load on the transmitting and receiving section 2a is 40%, a processing load on a sound ray data producing section 2b is 20%, and a processing load on image producing section 2c is 40%. Therefore, as the hardware resources are reduced, the processing load is decreased. As a result, power consumption can be reduced.

In this embodiment, since the ultrasound probe 2 is constituted as mentioned above, a data format is changed over to the optimum data format in consideration of a transmission rate, power consumption, and the specification of an ultrasound image diagnostic apparatus main body, and then the data can be wirelessly transmitted with the optimum data format. As a result, the ultrasound probe 2 is made excellent in general versatility.

Further, in this embodiment, the data format to be transmitted wirelessly can be changed arbitrarily by selecting operations in the changeover switch 21 and the ultrasound image diagnostic apparatus main body 1 Therefore, in the case where the apparatus main body applied with the ultrasound probe 2 in this embodiment is, for example, a socalled high-end machine applied with the high signal processing technique, a user can select a data format arbitrarily in consideration of a transmission rate, power consumption, diagnostic contents, etc.

As explained above, according to the embodiment of the present invention, the transmitting and receiving section 2a receives the ultrasound waves from an object, and acquires a reception signal of each of multiple channels. The beam forming section 206 performs the processing of beam forming for the reception signal of each of multiple channels. The image producing section 2c produces the ultrasound diagnostic image data to display an ultrasound diagnostic image based on the reception signals having been subjected to the processing of beam forming. The transmission data changeover control section 213 and the transmission data changeover switch 213a select one from at least two of a reception signal of each of multiple channels, sound ray data, and ultrasound diagnostic image data as a transmission target. The wireless transmission and reception section 215 transmits the transmission target selected by the transmission data changeover control section 213 and the transmission data changeover switch 213a. As a result, it becomes possible to apply various specifications of ultrasound image diagnostic apparatuses. Further, a data format is changed over to the optimum data format in consideration of a transmission rate, power consumption, and the specification of an ultrasound image diagnostic apparatus main body, and then the data can be transmitted with the optimum data format. That is, the ultrasound probe 2 is made excellent in general versatility.

Further, according to the embodiment of the present invention, the transmission data changeover control section 213 and the transmission data changeover switch 213a can select a transmission target in accordance with operation of the changeover switch 21. As a result, data can be transmitted with a data format changed over in accordance with the utilization purpose of a user, which results to be excellent in availability.

Furthermore, according to the embodiment of the present invention, the transmission data changeover control section 213 and the transmission data changeover switch 213a selects a transmission target in accordance with a remaining quantity of electricity in a battery 201. As a result, power consumption can be changed over in accordance with a remaining quantity of electricity in a battery, which results to be able to endure the examination conducted for a long time.

Moreover, according to the embodiment of the present invention, the transmission data changeover control section 213 and the transmission data changeover switch 213a selects a transmission target in accordance with a transmitting condition with the ultrasound image diagnostic apparatus main body 1 being the transmission destination of the transmission target. As a result, data of reception signals can be transmitted with a data format of a transmission rate changed over to be proper to a transmitting condition, the reliability of data to be transmitted can be enhanced, and further the transmission efficiency of data can be enhanced.

Further, according to the embodiment of the present invention, the wireless transmission and reception section 215 receives transmission signals from the ultrasound image diagnostic apparatus main body 1 which is a transmission destination of a transmission target. When the wireless transmission and reception section 215 receives a transmission target instructing signal to designate a transmission target from the ultrasound image diagnostic apparatus main body 1, the transmission data changeover control section 213 and the transmission data changeover switch 213a selects the transmission target corresponding to the received transmission target designating signal. As a result, data can be transmitted with a data format changed over in accordance with the utilization purpose of a user or the specification of the apparatus main body, and the ultrasound probe 2 is made excellent in usability and general versatility.

Furthermore, according to the embodiment of the present invention, the voltage and operation clock control section 217 selects a limiting target, to which supply of power is limited, from the beam forming section 206 and the image producing section 2c based on the transmission target selected by the transmission data changeover control section 213 and the transmission data changeover switch 213a, and limits supply of power for the selected limiting target. As a result, actions in the constitution not used in the processing can be stopped, thereby attaining to save electric power.

Moreover, according to the embodiment of the present invention, the voltage and operation clock control section 217 selects a lowering target, to which a frequency of an operation clock is lowered, from the beam forming section 206 and the image producing section 2c based on the transmission target selected by the transmission data changeover control section 213 and the transmission data changeover switch 213a, and changes a frequency of an operation clock supplied to the selected lowering target from a prescribed driving frequency to a prescribed standby frequency being a lower frequency than the driving frequency. As a result, power consumption in the constitution not used in the processing can be suppressed, thereby attaining to save electric power.

Herein, the description in the embodiment of the present invention is one example of the ultrasound image diagnostic apparatus according to the present invention, and the present invention is not limited to this example. The detailed constitutions and detailed operations of respective function sections which constitute the ultrasound image diagnostic apparatus can be changed appropriately.

Further, in the above embodiment, ID information which can specify the specification of an ultrasound image diagnostic apparatus main body is wirelessly transmitted to the ultrasound probe 2, and the ultrasound probe 2 may be configured to change transmission data corresponding to the specification of the apparatus main body specified by the ID information.

Furthermore, in the above embodiment, one of three data formats of the reception signals of each channel, sound ray data, and ultrasound diagnostic image data is configured to be selected as a transmission target. However, one of two data formats among the reception signals of each channel, sound ray data, and ultrasound diagnostic image data may be selected as a transmission target. In addition, it may be constituted that a data format different from the reception signals of each channel, sound ray data, and ultrasound diagnostic image data may be selected as a transmission target.

Moreover, in the above embodiment, image data in the B mode are produced as the ultrasound diagnostic image data. However, image data in the A mode and the M mode may be produced as the ultrasound diagnostic image data. Further, image data produced by the Doppler method may be used.

Moreover, in the above embodiment, transmission data are wirelessly transmitted between the ultrasound image diagnostic apparatus main body 1 and the ultrasound probe 2. However, transmission data may be transmitted through a cable. For example, it may be preferable to transmit data via serial transmission.

Moreover, in the above embodiment, the ultrasound probe which transmits and receives ultrasound waves is used. However, a receive-only ultrasound probe which conducts only receiving reflected ultrasound waves without transmitting transmission ultrasound waves.

What is claimed is:

1. A method for an ultrasound probe, which (i) is operable to (a) receive ultrasound waves from an object and to acquire a receiving signal of each of multiple channels, (b) adjust a phase of the receiving signal of each of the multiple channels and to sum the receiving signals, and (c) produce image data to display an ultrasound diagnostic image based on the summed receiving signals, and (ii) is operable to selectively transmit one of at least two which are selectable of (a) the receiving signal for each of the multiple channels, (b) the summed receiving signals, and (c) the image data, the method comprising:

transmitting the ultrasound waves to the object;

receiving reflected ultrasound waves reflected from the object to obtain the receiving signals;

selecting, as a transmission target, one of said at least two of the receiving signal for each of the multiple channels, the summed receiving signals, and the image data;

changing over a transmit data changeover switch which changes over electrical connection between (i) transmission paths of said at least two of the receiving signal for each of the multiple channels, the summed receiving signals, and the image data, and (ii) an antenna, so as to electrically connect the transmission path of the selected transmission target with the antenna; and transmitting the selected transmission target to an ultrasound image diagnostic apparatus main body in accordance with a connection state of the transmit data changeover switch;

wherein the method further comprises, adjusting a phase of the received signal for each of the multiple channels, and summing the received signals, when the summed receiving signals are selected as the transmission target;

wherein the method further comprises adjusting a phase of the received signal for each of the multiple channels, summing the received signals, and producing the image data for displaying on the display the ultrasound diagnostic image based on the summed signals, when the image data is selected as the transmission target;

wherein the transmission target is selected in consideration of at least one of a transmission rate, power consumption, a specification of the ultrasound image diagnostic apparatus main body, a transmission state, and a diagnostic content;

wherein, in a case in which the receiving signal for each of the multiple channels is selected as the transmission target, processing control is performed such that adjustment of the phase of the receiving signal of each of the multiple channels and summation of the receiving signals is not performed, and such that production of image data based on the receiving signals is not performed, and the transmitting of the selected transmission target to the ultrasound image diagnostic apparatus main body comprises transmitting the receiving signals which have not been subjected to phase adjustment and summation, and which have not been converted to image data; and wherein, in a case in which the summed receiving signals are selected as the transmission target, processing control is performed such that adjustment of the phase of the receiving signals of each of the multiple channels and summing of the receiving signals is performed, and such that production of image data based on the summed receiving signals is not performed, and the transmitting of the selected transmission target to the ultrasound image diagnostic apparatus main body comprises transmitting the summed receiving signals which have not been converted to image data.

2. The method according to claim 1, wherein the selecting of the transmission target is performed by operating a changeover switch which selects the transmission target, by an operator of the ultrasound probe; and wherein the transmit data changeover switch is changed over so as to electrically connect the transmission path of the selected transmission target with the antenna, in accordance with operation of the changeover switch by the operator.

3. The method according to claim 1, further comprising detecting a remaining quantity of electricity in a battery of the ultrasound probe;

wherein the selecting of the transmission target comprises selecting, as the transmission target, a first signal which is one of said at least two of the receiving signal for each of the multiple channels, the summed receiving signals, and the image data, when it is detected that the remaining quantity of electricity in the battery of the ultrasound probe is a first value or less, and selecting, as the transmission target, a second signal which has a smaller processing amount than the first signal, when it is detected that the remaining quantity of electricity in the battery is a second value or less.

4. The method according to claim 1, further comprising receiving a transmitting condition information signal from the ultrasound image diagnostic main body, the transmitting condition information signal indicating a transmitting condition of data transmission;

wherein the selecting of the transmission target comprises selecting, as the transmission target, a first signal which is one of said at least two of the receiving signal for each of the multiple channels, the summed receiving signals, and the image data, when the transmitting condition information signal indicates that the transmitting condition is a first condition or worse, and selecting, as the transmission target, a second signal which has a smaller necessary transmission rate than the first signal, when the transmitting condition information signal indicates that the transmitting condition is a second condition or worse, the second condition being worse than the first condition.

5. The method according to claim 1, further comprising:
receiving a transmission target designating signal from the ultrasound image diagnostic apparatus main body which is a transmission destination of the transmission target, wherein the selection of the transmission target is performed in accordance with the received transmission target designating signal.

6. The method according to claim 1, further comprising:
receiving specification information of the ultrasound image diagnostic apparatus main body which is a transmission destination of the transmission target, wherein the selection of the transmission target is performed in accordance with the received specification information.

7. The method according to claim 1, further comprising:
in accordance with the selected transmission target, limiting a supply of power in the ultrasound probe for at least one of (i) adjusting the phase of the receiving signal of each of the multiple channels and summing the receiving signals, and (ii) producing the image data to display the ultrasound diagnostic image based on the summed receiving signals.

8. The method according to claim 1, further comprising: in accordance with the selected transmission target, changing a frequency of an operation clock supplied for at least one of (i) adjusting the phase of the receiving signal of each of the multiple channels and summing the receiving signals, and (ii) producing the image data to display the ultrasound diagnostic image based on the summed receiving signals, from a prescribed driving frequency to a prescribed standby frequency that is lower than the driving frequency.

9. The method according to claim 1, wherein the receiving signal for each of the multiple channels, the receiving signals summed by the beam forming section, and the image data are different in data format and data size from each other.

10. The method according to claim 1, wherein the summed receiving signals are sound ray data.

11. A method for controlling an ultrasound probe which communicates with an ultrasound image diagnostic apparatus main body, the method comprising:
transmitting an ultrasound wave to an object;
receiving a reflected ultrasound wave reflected from the object;
selecting, as a transmission target to be transmitted to the ultrasound image diagnostic apparatus main body from the ultrasound probe, a type of data produced in the ultrasound probe, from at least two types of data including a first type of data and a second type of data different from the first type, wherein a processing amount required to produce the first type of data is less than a processing amount required to produce the second type of data, and wherein the second type of data is generated from the first type of data;
changing over a transmit data changeover switch which changes over electrical connection between (i) transmission paths of said at least two types of the data produced in the ultrasound probe, and (ii) an antenna, so as to electrically connect the transmission path of the selected transmission target with the antenna;
producing data based on the received reflected ultrasound wave depending on the selected type of data; and
transmitting the produced data to the ultrasound image diagnostic apparatus main body in accordance with a connection state of the transmit data changeover switch; wherein the transmission target is selected in consideration of at least one of a transmission rate, power consumption, a specification of the ultrasound image diagnostic apparatus main body, a transmission state, and a diagnostic content; and
wherein, in a case in which the first type of data is selected as the transmission target, processing control is performed such that processing to produce the second type of data is not performed on the first type of data, and the transmitting of the selected transmission target comprises transmitting the first type of data which has not been subjected to the processing to produce the second type of data,
wherein each of the types of data of which processing amounts are different from each other is one of (i) a received signal of each of multiple channels, (ii) a signal obtained by adjusting a phase of the received signal of each of the multiple channels and summing the received signals, and (iii) image data for displaying on a display an ultrasound diagnostic image based on the summed signals,
wherein the selecting of the transmission target is performed by operating a changeover switch which selects the transmission target, by an operator of the ultrasound probe, and
wherein the transmit data changeover switch is changed over so as to electrically connect the transmission path of the selected transmission target with the antenna, in accordance with operation of the changeover switch by the operator.

12. The method for controlling the ultrasound probe of claim 11 further comprising:
acquiring the received signal from the reflected ultrasound wave for each of the multiple channels, when the selected type of data is the received signal of each of the multiple channels;
acquiring the received signal from the reflected ultrasound wave for each of the multiple channels, adjusting a phase of the received signal for each of the multiple channels, and summing the received signals, when the selected type of data is the summed signals; and
acquiring the received signal from the reflected ultrasound wave for each of the multiple channels, adjusting a phase of the received signal for each of the multiple channels, summing the received signals, and producing the image data for displaying on the display the ultrasound diagnostic image based on the summed signals, when the selected type of data is the image data.

13. The method according to claim 11, further comprising detecting a remaining quantity of electricity in a battery of the ultrasound probe;
wherein the selecting of the transmission target comprises selecting, as the transmission target, a first signal which is one of said at least two types of data, when it is detected that the remaining quantity of electricity in the battery is a first value or less, and selecting, as the transmission target, a second signal which has a smaller processing amount than the first signal, when it is detected that the remaining quantity of electricity in the battery is a second value or less.

14. The method according to claim 11, further comprising receiving a transmitting condition information signal from the ultrasound image diagnostic main body, the transmitting condition information signal indicating a transmitting condition of data transmission;
wherein the selecting of the transmission target comprises selecting, as the transmission target, a first signal which is one of said at least two types of data, when the transmitting condition information signal indicates that the transmitting condition is a first condition or worse, and selecting, as the transmission target, a second signal which has a smaller necessary transmission rate than the first signal, when the transmitting condition information signal indicates that the transmitting condition is a second condition or worse, the second condition being worse than the first condition.

15. The method according to claim 11, further comprising:
receiving a transmission target designating signal from the ultrasound image diagnostic apparatus main body which is a transmission destination of the transmission target,
wherein the selection of the transmission target is performed in accordance with the received transmission target designating signal.

16. The method according to claim 11, further comprising:

receiving specification information of the ultrasound image diagnostic apparatus main body which is a transmission destination of the transmission target,
wherein the selection of the transmission target is performed in accordance with the received specification information.

* * * * *